United States Patent [19]

Sanfilippo et al.

[11] Patent Number: 5,493,059
[45] Date of Patent: Feb. 20, 1996

[54] PROCESS FOR PREPARING TERTIARY ALKYL ETHERS AND APPARATUS FOR REACTIVE DISTILLATION

[75] Inventors: Domenico Sanfilippo, Paullo; Maria Lupieri, Milan; Francesco Ancillotti, San Donato Milanese, all of Italy

[73] Assignees: Eniricerche SpA; Snamprogetti SpA; Ecofuel SpA, all of Milan, Italy

[21] Appl. No.: 68,601

[22] Filed: May 27, 1993

Related U.S. Application Data

[63] Continuation of Ser. No. 730,463, Jul. 16, 1991, abandoned.

[30] Foreign Application Priority Data

Aug. 1, 1990 [IT] Italy ........................ 21160/90

[51] Int. Cl.[6] .................................................. C07C 41/06
[52] U.S. Cl. ................................ 568/697; 422/191
[58] Field of Search ............................................. 568/697

[56] References Cited

U.S. PATENT DOCUMENTS

| 4,471,154 | 9/1984 | Franklin . | |
| 4,847,430 | 7/1989 | Quong et al. | 568/697 |
| 4,847,431 | 7/1989 | Nocca et al. . | |
| 5,237,109 | 8/1993 | Patton et al. | 568/697 |
| 5,243,102 | 9/1993 | Marker et al. | 568/697 |

*Primary Examiner*—Howard T. Mars
*Attorney, Agent, or Firm*—Rogers & Wells

[57] ABSTRACT

A process for the preparation of tertiary alkyl ethers, in particular methyl-tert.-butyl-ether (MTBE), from iso-olefins and aliphatic alcohols by means of a fractionation tower is disclosed, in which the main characteristic of the fractionation tower consists in that the reaction mixture is caused to flow through the catalytic trays in transversal direction relatively to the axis of the same fractionation tower.

9 Claims, 3 Drawing Sheets

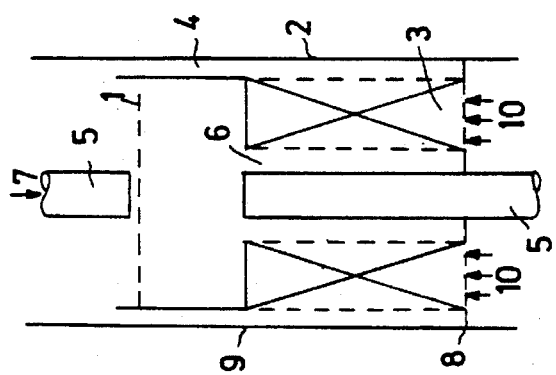
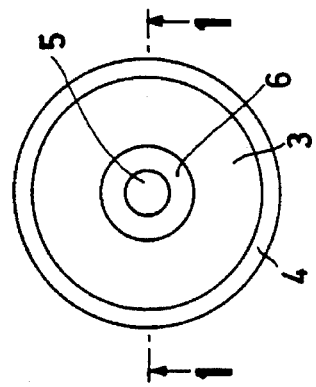
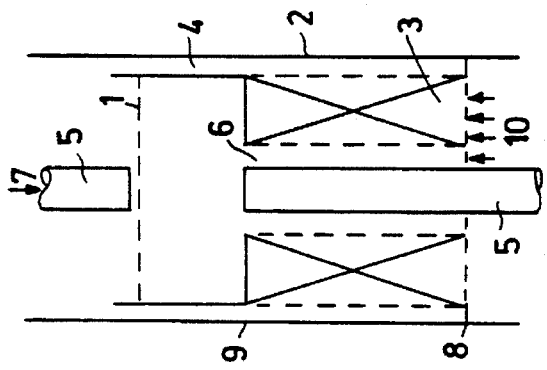
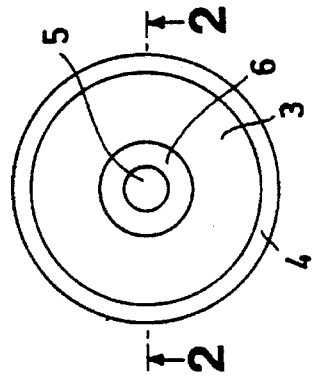
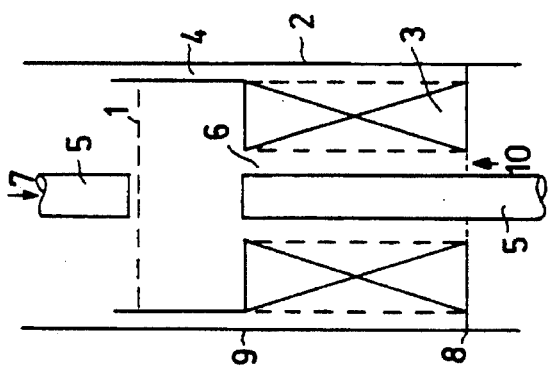
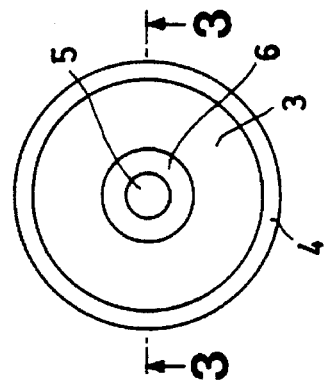
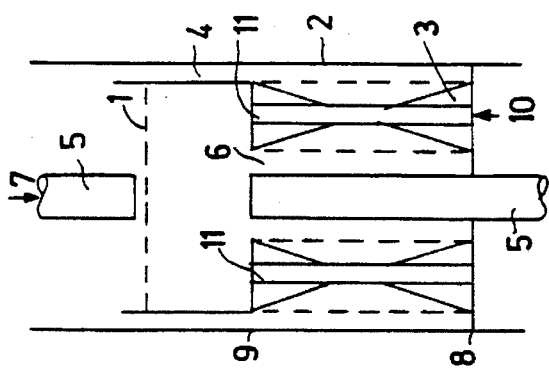
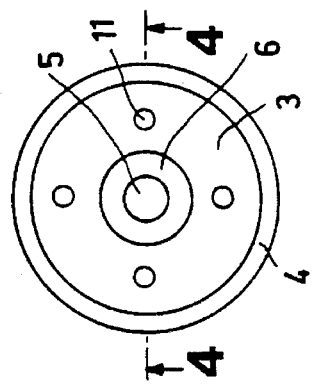

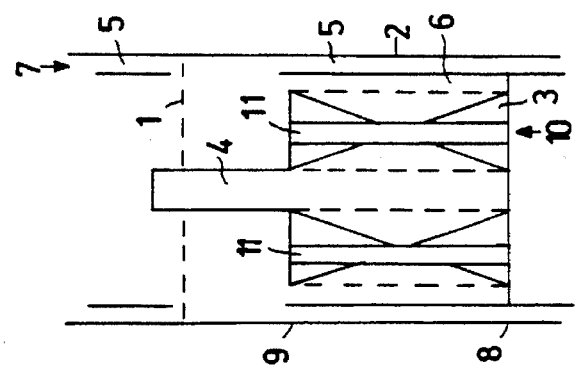
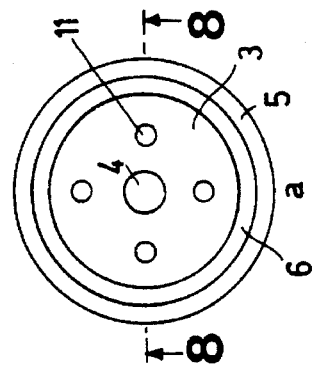
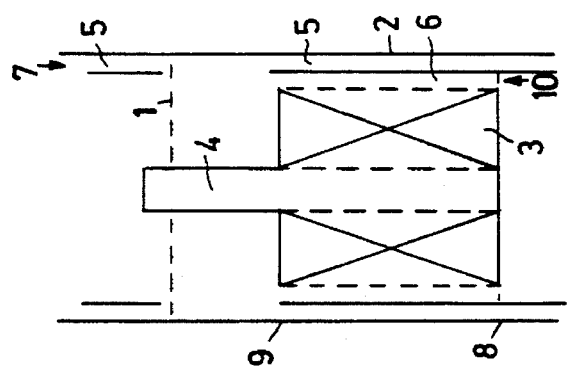
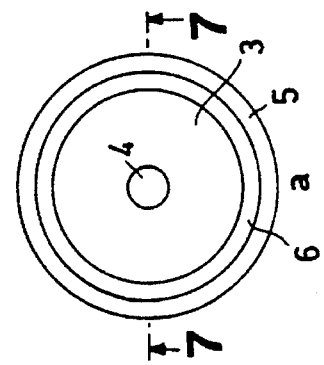
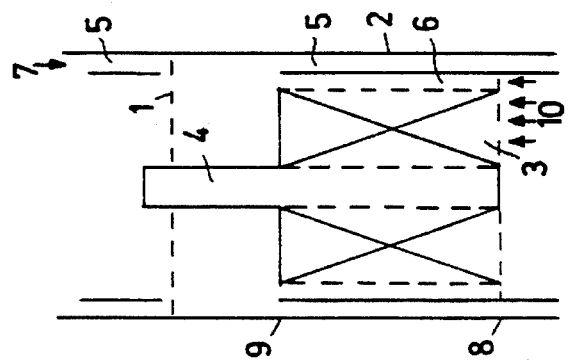
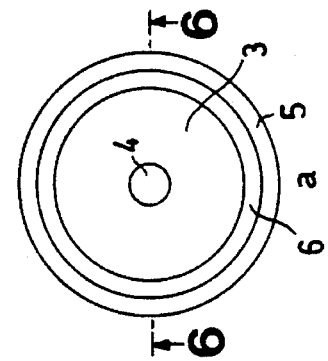
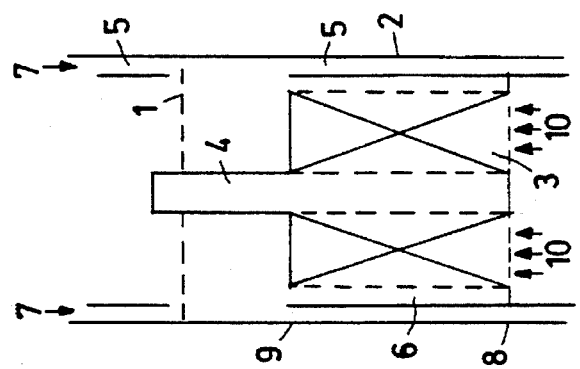
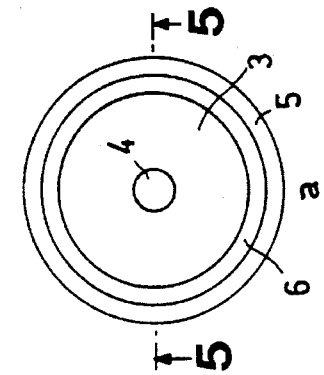

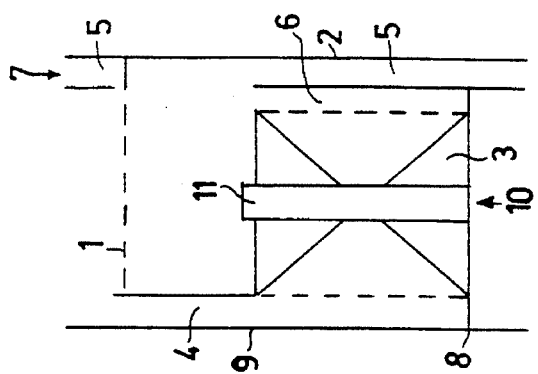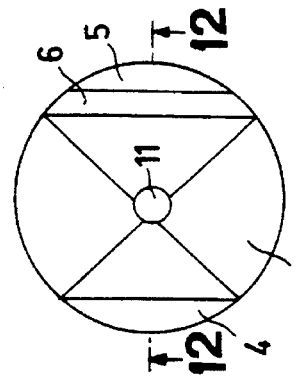
Fig.12  Fig.12A
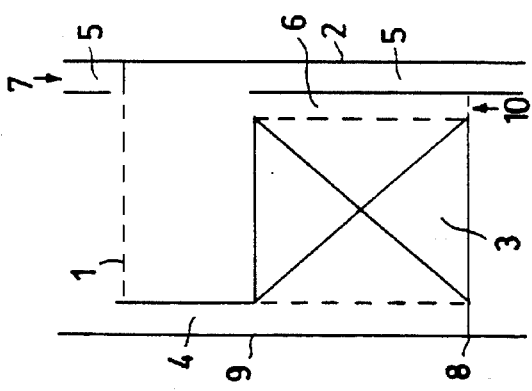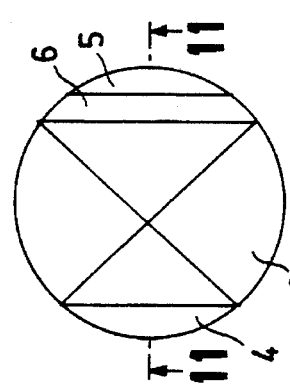
Fig.11  Fig.11A
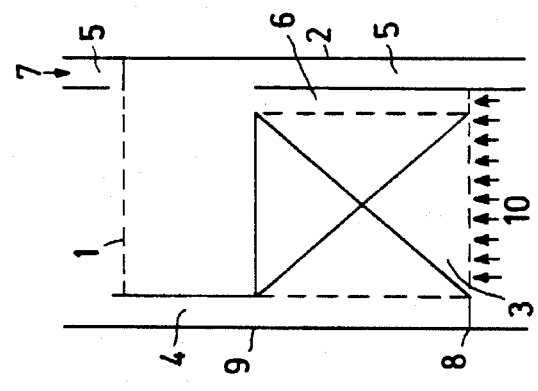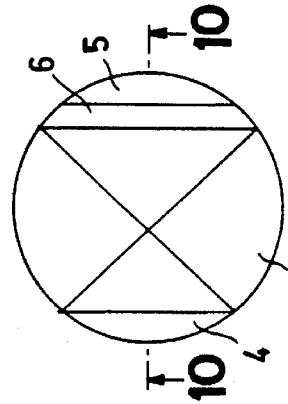
Fig.10  Fig.10A
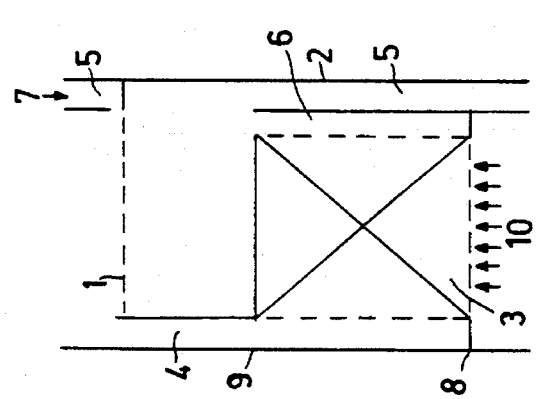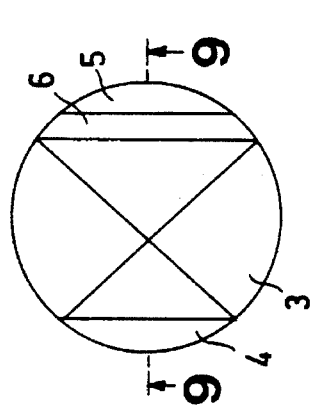
Fig.9  Fig.9A

PROCESS FOR PREPARING TERTIARY ALKYL ETHERS AND APPARATUS FOR REACTIVE DISTILLATION

This application is a continuation of application Ser. No. 07/730,463, filed Jul. 16, 1991 and now abandoned.

The present invention relates to a process for preparing tertiary alkyl ethers from iso-olefins and aliphatic alcohols by means of a reactive distillation and an apparatus suitable for the intended purpose.

In the following, in the instant disclosure reference is made sometimes, for the sake of simplicity, to the preparation of methyl-tert.-butyl-ether (MTBE), it having anyway to be understood that the process is fully valid also for the preparation of all the other tert.-alkyl ethers, it being considered that the differences between the boiling points of the components and of the products are all of the same order of magnitude.

The process according to the present invention is applicable to all those cases in which the reaction conditions are compatible with a distillation, and in which one or more reactant(s) has(have) boiling points different from one or more reaction products.

Methyl-tert.-butyl-ether (MTBE) is obtained at the industrial level by causing isobutene, contained in a $C_4$ hydrocarbon stream, to react with methanol in the presence of a catalyst, generally constituted by sulfonated styrene-divinylbenzene resins, at temperatures which may vary from room temperatures up to approximately 100° C. (U.S. Pat. No. 3,979,461; IT 1,012,686).

From Italian patent 1,137,527 issued to the same Applicant names, causing the reaction of formation of MTBE to occur and separating said MTBE reaction product from the hydrocarbons and compounds which accompany it, in one single apparatus with fractionation trays, in which some trays are equipped with catalyst beds formed by spherical catalyst particles, is known.

In particular, in said patent the use is shown of a series of catalytic regions with an upwards flowing stream of liquid and vapour through each catalytic bed, in which the catalyst is always covered by a liquid head.

Unfortunately, the process disclosed in said reference suffers, in some cases, from some drawbacks, due to the fact that, under particular process conditions, the catalytic bed may lead to too high pressure drops, in particular in case of too thick catalytic beds.

In a recent patent, i.e., U.S. Pat. No. 4,847,431; it is stated that most of these fluid-dynamic problems can be solved causing the liquid to flow downwards through the catalytic bed, while maintaining an always rising flow of the vapour stream.

Notwithstanding this expedient, the pressure drops through the bed may anyway be still relatively high.

The present Applicants have found now that by causing the liquid phase to flow in the transversal direction through the catalytic bed, the pressure drops can be effectively reduced.

The process according to the present invention for preparing tertiary alkyl ethers, in particular methyl-tert.-butyl-ether (MTBE) from iso-olefins and aliphatic alcohols, comprises the following steps:

the hydrocarbonaceous feedstock containing the iso-olefin and, possibly, a portion of the alifatic alcohol, is fed to a fractionation tower fitted with trays, wherein some of said trays are equipped with catalyst beds, constituted, e.g., by sulfonated styrene-divinyl-benzene resins, and are possibly separated from each other by groups of, or single, conventional distillation trays (or perforated trays, or valve trays, or bubble-cap trays);

at least a portion of the aliphatic alcohol is fed, alone, at a point in the nearby of the head of the fractionation tower;

said iso-olefin is caused to react with said alcohol on the catalytic bed bearing trays, with said catalytic beds being submerged in the reactant mixture;

the ether product is separated from the other compounds both on the distillation trays and on the catalytic bed bearing trays, with substantially pure ether being obtained as the bottom product stream; and the unreacted hydrocarbons from the feedstock and, possibly, the alcohol—as azeotropic mixtures with said hydrocarbons—being obtained as the overhead stream, characterized in that in said tray-fitted fractionation tower, of substantially vertical, cylindrical shape, inside which the formation of the tert.-alkyl-ether and the separation of said tert.-alkyl-ether from the accompanying hydrocarbons and compounds, is carried out, the liquid reactant mixture flows through the catalytic beds placed on the catalytic trays in the cross direction relatively to the axis of the same fractionation tower.

The term "cross" is meant to also encompass the term "radial relatively to the catalytic beds". In particular, the flow of the liquid phase can take place through the catalytic bed from the outside inwards, i.e., from the external side wall of the same bed, towards the internal wall; or from the inside outwards, i.e., from the internal side wall of the same bed, towards the external wall, or from one side end towards the other side end, i.e., from the side end of the bed, close to the downcomer which conveys the liquid from the upper tray, towards the opposite wall of the same catalytic bed.

The process according to the present invention is carried out at a pressure comprised within the range of from 200 to 3000 kPa, preferably of from 500 to 2000 kPa, at a temperature comprised within the range of from room temperature to 200° C., preferably of from 45° C. to 150° C.

The reflux rate of the fractionation tower should be preferably kept comprised within the range of from 0.5 to 15, more preferably of from 1 to 10.

The catalyst is in the form or grains, cylindrical bodies, spherical bodies, and, more generally, consists of particles with any shapes as regarded to be the most advantageous for its production and use. The catalyst may also be of small size, such as, e.g., spheroidal particles with a diameter comprised within the range of from 0.5 to 1 mm. A further object of the present invention is an apparatus suitable for use in any processes of reactive distillation, such as, e.g., in those processes in which reactions are carried out, which involve chemical equilibrium in which the products and the reactants are easily separated from one another, in that they have such volatility characteristics which render them capable of being easily and advantageously—from an industrial viewpoint—separated.

In particular, such an apparatus is suitable for the processes for the preparation of tertiary alkyl ethers, such as, e.g., MTBE, ETBE (ethyl-tert.-butyl-ether), TAME (tert.-alkyl-methyl-ether), for preparing cumene from propene and benzene, for preparing isobutene from MTBE, for the alkylation of isoparaffins with olefins.

The apparatus for reactive distillation, comprising one or more region(s) essentially containing one catalytic tray, and, possibly, a conventional distillation tray, is characterized in that the catalytic tray is constituted by one or more element(s), each comprising a catalytic bed, two downcomers and a non-catalytic chamber, with the catalytic bed being provided of a suitable support capable of allowing the liquid reactant mixture fo flow through the same bed, in a transversal direction relatively to the axis of the same apparatus, and to retain the catalyst charged to it.

BRIEF DESCRIPTION OF THE DRAWINGS

The invention is disclosed now in greater detail by referring to the accompanying figures, which show non-limitative forms of practical embodiment.

In particular, said figures relate to the different shapes which the catalytic regions of the fractionation tower may have, which shapes will be such as to make it possible a flow of the reaction mixture in the transversal direction, in particular in the radial direction, to be obtained through the catalytic beds.

For the sake of simplicity, in said figures catalytic trays are reported, which are constituted by one single element.

In FIGS. 1 and 1(A), a region of the apparatus is depicted, which comprises one distillation tray of conventional type (1), which may be a perforated tray, a valve-tray or a bubble-cap tray, and one catalytic tray (2), which comprises a fixed catalytic bed (3), two downcomers (4) and (5), and a non-catalytic chamber (6).

The liquid reactant mixture (7) flows downwards through the downcomer (5) to the distillation tray (1), from which it subsequently flows downwards towards the catalytic tray (2) through the downcomer (4), flowing through the catalytic bed (3) in a transversal direction relatively to the axis of the apparatus, from the external side wall of the same bed, towards the innermost wall of said bed.

After flowing through the catalytic bed (3), the liquid reactant mixture flows into the non-catalytic chamber (6) and flows, through the downcomer (5), into a lower region of the apparatus, which, in its turn, may be possibly equipped with one or more distillation tray(s), or one or more catalytic tray(s), or a combination of one or more catalytic tray(s) and one or more distillation tray(s).

The bottom portion (8) of the catalytic tray is only perforated in its region corresponding to the catalyst containing bed (3), whilst the upper portion (9) of said plate is preferably closed or perforated in its region corresponding to said bed, and is open in its region corresponding to the non-catalytic chamber (6).

The vapour (10) rises flowing through the bottom portion (8), coming into contact with a portion of the catalytic bed (3), leaving the non-catalytic chamber (6), and finally reaching the distillation tray (1).

In FIGS. 2(a) and (b), a region of the apparatus is depicted, which is substantially analogous to the portion schematically shown in FIGS. 1 and 1(A), except that the portion (8) of the reactor portion of the tray (2) is also perforated in its region corresponding to the non-catalytic chamber (6). In that way, a portion of the vapour (10) bypasses the catalytic bed.

In FIGS. 3 and 3(A), a region of the apparatus is depicted, which is substantially analogous to the portion schematically shown in FIGS. 2 and 2(A), except that the bottom portion (8) is only perforated in its region corresponding to the non-catalytic chamber (6). In that way, all vapour (10) bypasses the catalytic bed.

In FIGS. 4(a) and (b), a region of the apparatus is depicted, which is substantially analogous to the regions schematically shown in the preceding Figures, except that inside the catalytic bed (3) tubes (11) are provided, through which the vapour (10) which, from the tray underneath the tray (2) rises towards the tray (1). The portion (8) is not perforated, but in its region corresponding to said tubes, in order to enable vapour (10) to rise through.

In FIGS. 5 and 5(A), FIGS. 6 and 6(A), FIGS. 7 and 7(A), and FIGS. 8 and 8(A) regions of the apparatus are shown, which are substantially analogous to those respectively schematized in FIGS. 1 and 1(A), FIGS. 2 and 2(A), FIGS. 3 and 3(A), and FIGS. 4 and 4(A), except that the liquid reactant mixture flows through the catalytic bed (3) from the inner side wall of the bed towards the external side wall of said bed, with the flowing direction being transversal relatively to the axis of the same apparatus.

After flowing through the catalytic bed (3), the liquid reactant mixture flows into the non-catalytic chamber (6) and, through the downcomer (5) sinks into a lower region of the apparatus, which lower region, in its turn, may be possibly equipped with one or more distillation tray(s) and one or more catalytic tray(s), or a combination of one or more catalytic tray(s) and one or more distillation tray(s).

In FIGS. 9 and 9(A), FIGS. 10 and 10(A), FIGS. 11 and 11(A), and FIGS. 12 and 12(A) regions of the apparatus are shown, which are substantially analogous to those respectively schematized in FIGS. 1, 2, 3 and 4 or in FIGS. 1 and 1(A), FIGS. 2 and 2(A), FIGS. 3 and 3(A), and FIGS. 4 and 4(A) or in FIGS. 5 and 5(A), FIGS. 6 and 6(A), FIGS. 7 and 7(A), and FIGS. 8 and 8(A), except that the liquid reactant mixture flows through the catalytic bed (3) with its flowing direction being transversal relatively to the axis of the same apparatus, from one side end to the other side end, i.e., from the side wall close to the downcomer which conveys the liquid from the upper portion of the apparatus, to the opposite side of the same catalytic bed.

If on a same catalytic tray a plurality of elements are used, one or more downcomer(s) may also be shared by a plurality of said elements.

EXAMPLE

By feeding a hydrocarbonaceous feedstock consisting of saturated and unsaturated $C_4$ hydrocarbons containing 15% by weight of isobutene, to an apparatus of the same type as schematically shown in the figures, equipped with a plurality of catalytic beds and containing, as the catalyst, sulfonated styrenedivinylbenzene resin, and with distillation trays, by operating according to the process of the present invention under a pressure of approximately 10 bars, with a reflux rate of 1 and at temperatures comprised within the range of from 65° C. to 140° C., a conversion of isobutene into MTBE higher than 95% was obtained.

The bottom MTBE stream is obtained with a high purity; the overhead product is substantially free from MTBE.

Such a result was obtained by installing one distillation tray between two catalytic trays.

We claim:

1. Process for preparing tertiary alkyl ethers from iso-olefins and aliphatic alcohols, comprising the following steps:

feeding a feedstock containing at least the iso-olefin to a fractionation tower fitted with trays, wherein some of said trays are equipped with fixed catalyst beds;

feeding at least a portion of the aliphatic alcohol at a point in the nearby of the head of the fractionation tower;

reacting said iso-olefin with said alcohol on the fixed spaced catalyst bed bearing trays, with said fixed catalyst beds being submerged in the reactant mixture, to form a tert.-alkyl-ether product;

separating the tert.-alkyl-ether product from any unreacted hydrocarbon, unreacted alcohol and azeotropic mixtures of alcohol and hydrocarbon as substantially pure ether obtained as a bottom product stream; and obtaining any unreacted hydrocarbons, unreacted alcohols, and azeotropic mixtures as an overhead stream, wherein in said tray-fitted fractionation tower the liquid reactant mixture flows through the fixed spaced catalytic beds in the catalytic trays in the cross direction relative to the axis of the fractionation tower.

2. Process according to claim 1, wherein the reactant mixture flows in the radial direction relative to the axis of the tower.

3. Process according to claim 1, wherein the reactant mixture flows in the transverse direction relative to the axis of the tower, from one side end to the other side end, of the catalytic beds arranged on the catalytic trays.

4. Process according to claim 1, wherein the reaction forming the tert.-alkyl-ether and the separation thereof is carried out at a pressure within the range of from 200 to 3000 kPa, and at a temperature within the range of from room temperature to 200° C.

5. Process according to claim 4, wherein the pressure is within the range of from 500 to 2000 kPa and the temperature is within the range of from 45° to 150° C.

6. Process according to claim 1, wherein the tertiary alkyl ether is methyl-tert.-butyl-ether (MTBE).

7. Process according to claim 1, wherein a portion of the aliphatic alcohol is fed along with the feedstock of the iso-olefin.

8. Process according to claim 1, wherein the trays equipped with catalyst beds are separated from each other by at least one conventional distillation tray.

9. Process according to claim 1, wherein the fractionation tower is cylindrical in shape and vertically disposed.

* * * * *